(12) United States Patent
Goto et al.

(10) Patent No.: US 9,541,531 B2
(45) Date of Patent: Jan. 10, 2017

(54) DETECTOR FOR LIQUID CHROMATOGRAPHY

(71) Applicant: HITACHI HIGH-TECHNOLOGIES CORPORATION, Tokyo (JP)

(72) Inventors: Yusuke Goto, Tokyo (JP); Masao Kamahori, Tokyo (JP); Kiyotoshi Mori, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 279 days.

(21) Appl. No.: 14/477,989

(22) Filed: Sep. 5, 2014

(65) Prior Publication Data

US 2015/0090014 A1   Apr. 2, 2015

(30) Foreign Application Priority Data

Sep. 30, 2013 (JP) .................................. 2013-204590

(51) Int. Cl.
*G01N 30/74* (2006.01)
*G01N 30/86* (2006.01)

(52) U.S. Cl.
CPC ........... *G01N 30/74* (2013.01); *G01N 30/8641* (2013.01)

(58) Field of Classification Search
CPC ........ G01N 30/74; G01N 21/33; G01N 21/35; G01N 30/8641
See application file for complete search history.

(56) References Cited

U.S. PATENT DOCUMENTS

| 5,173,742 A * | 12/1992 | Young | G01N 30/74 |
| | | | 250/373 |
| 6,118,536 A * | 9/2000 | Sakamoto | G01N 21/19 |
| | | | 356/364 |
| 6,339,472 B1 * | 1/2002 | Hafeman | G01J 3/08 |
| | | | 356/433 |

(Continued)

FOREIGN PATENT DOCUMENTS

| JP | 60-011165 A | 1/1985 |
| JP | 7/12726 A | 1/1995 |

(Continued)

OTHER PUBLICATIONS

Japanese Office Action received in corresponding Japanese Application No. 2013-204590 dated Oct. 4, 2016.

*Primary Examiner* — Francis Gray
(74) *Attorney, Agent, or Firm* — Mattingly & Malur, PC

(57) ABSTRACT

A detector for liquid chromatography has light sources that generate light in an ultraviolet region and in a near-infrared region; a flow cell, through which sample liquid flows; an optical system to let light generated from the light sources become incident on the flow cell concurrently; a detection element that detects light in the ultraviolet region that passes through the flow cell; a detection element that detects light in the near-infrared region that passes through the flow cell; and an arithmetic operation part that performs arithmetic operation of a first signal value obtained from the detection element and of a second signal value obtained from the detection element. The arithmetic operation part combines the first signal value and the second signal value to calculate a signal value with a reduced baseline fluctuation resulting from a mobile phase during a gradient analysis.

11 Claims, 14 Drawing Sheets

(56) References Cited

U.S. PATENT DOCUMENTS

2010/0291691 A1\* 11/2010 Sugiyama .............. G01N 21/31
                                                                    436/67
2015/0096349 A1\* 4/2015 Johnson ................... G01N 1/38
                                                                    73/23.37

FOREIGN PATENT DOCUMENTS

| JP | 2006-275873 A | 10/2006 |
| JP | 2007-315942 A | 12/2007 |

\* cited by examiner

Detection result at first detection element

Detection result at second detection element

Combination of detection result at first detection element and detection result at second detection element Detection result at first detection element Detection result at second detection element Combination of detection result at first detection element and detection result at second detection element

DETECTOR FOR LIQUID CHROMATOGRAPHY

CLAIM OF PRIORITY

The present application claims priority from Japanese patent application JP 2013-204590 filed on Sep. 30, 2013, the content of which is hereby incorporated by reference into this application.

BACKGROUND

Technical Field

The present invention relates to a detector for liquid chromatography and a method to correct a detection signal thereof.

Background Art

In general-purpose liquid analyzers including a liquid chromatograph, absorbance detectors have been widely used because of its high detection sensitivity and user-friendliness. Especially an ultraviolet wavelength band that is short wavelengths of 300 nm or less includes excitation wavelengths of various functional groups in organic compounds, and so all industrially-useful organic compounds can be a detection target in such a wavelength band. Specifically transitions of $\sigma \rightarrow \sigma^*$, $n \rightarrow \sigma^*$, $n \rightarrow \pi^*$ and $\pi \rightarrow \sigma^*$ correspond to electron transitions in this wavelength region, in which hydroxyl groups, carboxyl groups, carbonyl groups and ether groups, for example, have absorption peaks, and so ultraviolet-region absorbance detectors have a potential to be a detector having universal responsivity, and so have been studied repeatedly so far. Such an ultraviolet-region absorbance detector, however, has a problem that its baseline changes greatly when a gradient analysis is applied in the liquid chromatographic field, thus failing to yield a good chromatogram. The gradient analysis is a method of successively changing the concentration of the mobile phase from aqueous solution to organic-solvent based solution such as methanol or acetonitrile. Since such an organic solvent has a strong absorption in the ultraviolet wavelength band compared with water, the baseline changes with the change in composition ratio of the organic solvent during a gradient analysis, and so the applicable range thereof is limited.

To solve this problem, the following correction method has been proposed (Patent Document 1). Firstly, a blank sample is introduced to acquire a baseline fluctuation value resulting from the mobile phase only. Next, a sample is introduced to acquire a signal fluctuation value resulting from the sample and the mobile phase. Finally, a correction factor is multiplied, and a difference therebetween is calculated, thus reducing a baseline fluctuation resulting from the mobile phase.

RELATED ART DOCUMENT

Patent Document

Patent Document 1: JP S60-11165 A

SUMMARY

The conventional method cannot reduce a baseline fluctuation resulting from the mobile phase during a gradient analysis in real time. Further, every time the analysis method (e.g., types of a mobile phase, a used column, the flow rate or the temperature of a column), a baseline fluctuation value resulting from the mobile phase has to be found, which is a disadvantage for a user because the number of steps increases.

In view of the problems, it is an object of the present invention to provide an ultraviolet-region absorbance detector capable of reducing a baseline fluctuation resulting from the mobile phase during a gradient analysis in real time.

A detector for liquid chromatography according to the present invention, includes: a first light source that generates light in an ultraviolet region (100 nm or more and 400 nm or less); a second light source that generates light in a near-infrared region (800 nm or more and 3,000 nm or less); a flow cell, through which sample liquid flows; an optical system to let light generated from the first light source and light generated from the second light source incident on the flow cell concurrently; a first detection element that detects light in the ultraviolet region that passes through the flow cell; a second detection element that detects light in the near-infrared region that passes through the flow cell; and an arithmetic operation part that performs arithmetic operation of a first signal value obtained from the first detection element and of a second signal value obtained from the second detection element.

The sample liquid may include water as one component, and the water has concentration that changes successively with time.

The arithmetic operation part may combine the first signal value and the second signal value to reduce a baseline fluctuation resulting from a mobile phase during a gradient analysis.

Preferably, light in the ultraviolet region has a wavelength band of 300 nm or less where absorption peaks of organic substances exist, and light in the near-infrared region has a wavelength band of 1,100 nm or more that is the limitation of a sensing wavelength of a silicon photodiode. The detector for liquid chromatography preferably further includes a third detection element to monitor intensity of light in the ultraviolet region before entering the flow cell, and a fourth detection element to monitor intensity of light in the near-infrared region before entering the flow cell. Light in the ultraviolet region and in the near-infrared region may be monochromatic light of single wavelength subjected to splitting, or light including a continuous wavelength not subjected to splitting. It is desirable to design so that light in the ultraviolet region and light in the near-infrared region proceed along a same optical path to the extent possible.

Based on the first signal value from the first detection element and the second signal value from the second detection element obtained by the above method, a baseline fluctuation resulting from the mobile phase is reduced. For instance, linear transformation of the first signal value and the second signal value can reduce a fluctuation value. The signal value is not limited to scalar quantity, which may be vector quantity, and a method may be to perform linear transformation or matrix operation of a first signal value vector and a second signal value vector including vector data having information on a plurality of wavelengths for correction. In that case, the detection element may be an array-type detection element having a plurality of elements, which may be combined with light subjected to splitting to be a method of combining a plurality of signal values having information on multiple-wavelengths. Specific examples of the arithmetic operation to reduce a baseline fluctuation resulting from the mobile phase include Expressions 1, 2 and 3 described later.

While water has a property of weak absorption in the ultraviolet region and strong absorption in the near-infrared region, organic solvent such as methanol has a property of strong absorption in the ultraviolet region and weak absorption in the near-infrared region. Organic compounds such as sugars and polymers as a sample fortunately have a feature of very weak absorption in the near-infrared region and very strong absorption in the ultraviolet region. Then, light in the ultraviolet region and light in the near-infrared region are introduced into the flow cell channel concurrently, and an absorbance detector is configured to include a detection element suitable for each wavelength band, whereby a synthesized signal value of a signal value resulting from the mobile phase and a signal value resulting from the sample can be detected with light in the ultraviolet light, and a signal value resulting from the mobile phase only can be detected with light in the near-infrared region. Combination of these signal values can reduce a baseline fluctuation resulting from the mobile phase at any analysis condition in real time.

Problems, configurations, and advantageous effects other than those described above will be made clear by the following description of embodiments.

DETAILED DESCRIPTION OF THE EMBODIMENT(S)

The following describes embodiments of the present invention, with reference to the drawings.

Figure 1:
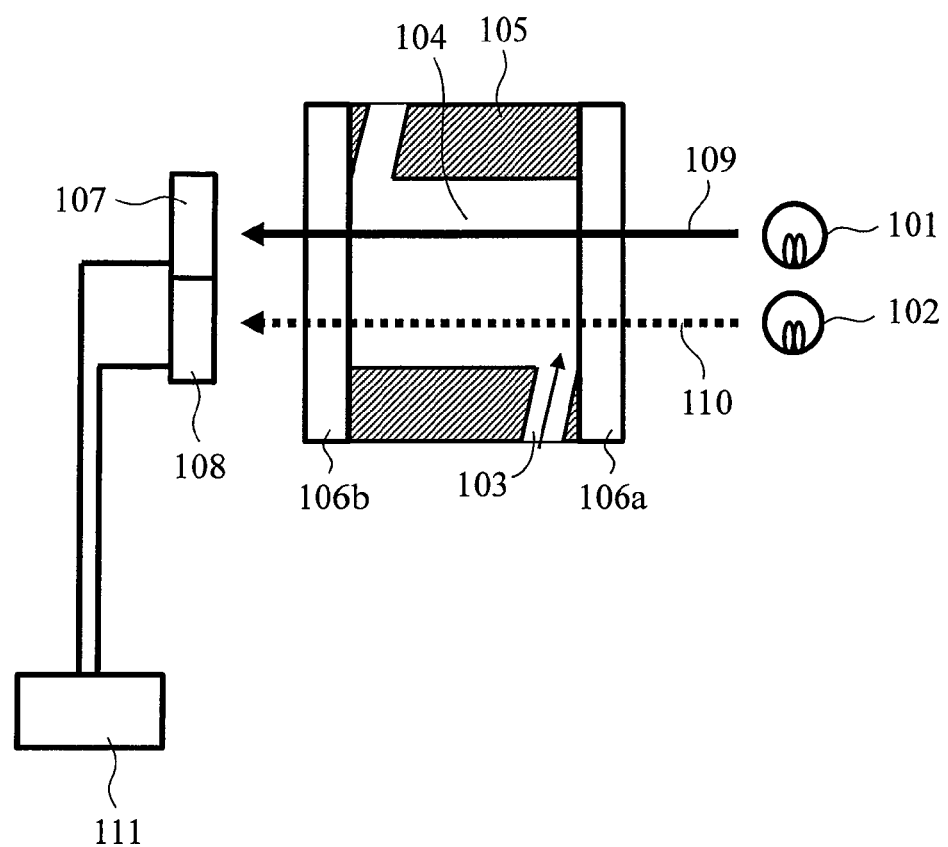
FIG. 1 schematically illustrates an embodiment of a detector for liquid chromatography according to the present invention.

FIG. 1 schematically illustrates an embodiment of a detector for liquid chromatography according to the present invention. The detector for liquid chromatography of the present invention includes: a first light source 101 for ultraviolet-region; a second light source 102 for near-infrared region; a flow cell 105 having a channel 104 through which sample liquid 103 containing water as a component of eluent and having concentration that successively changes passes; flow cell windows 106a and 106b on the incoming side and the outgoing side; a first detection element 107 for ultraviolet region; a second detection element 108 for near-infrared region; and an arithmetic operation part 111 to calculate a signal value obtained from the first detection element 107 and the second detection element 108. Ultraviolet light 109 generated from the first light source and near-infrared light 110 generated from the second light source pass through the channel 104 in the flow cell 105 concurrently. In the present specification, the ultraviolet region is defined as 100 nm or more and 400 nm or less, and the near-infrared region is defined as 800 nm or more and 3,000 nm or less.

The first light source 101 for ultraviolet region desirably is a light source that can generate light in a wavelength region of 300 nm or less. Exemplary light sources having a wide-range wavelength region include a deuterium lamp, a mercury lamp, a xenon flash lamp, and a metal halide lamp preferably, and exemplary light sources having a narrow-range wavelength region include an excimer lamp and a laser emission diode (LED) or a laser for ultraviolet region, which can simplify the optical system without a spectroscope. The second light source 102 for near-infrared region desirably is a light source that can generate light in a wavelength region of 1,100 nm or more. Exemplary light sources having a wide-range wavelength region include a tungsten lamp, a Glover lamp and a nichrome wire heater lamp desirably.

In the present invention, light in a near-infrared region is used to detect a concentration change of water in the mobile phase, and so the light source used may be any light that generates light of wavelengths of 900 to 950 nm, 1,100 to 1,150 nm, 1,340 to 1,480 nm, 1,800 to 2,100 nm and 2,500 to 2,800 nm. Table 1 shows the central wavelength of a vibration band in association with the quantum number at each level of symmetrical stretch vibration, bending vibration, and antisymmetric stretch vibration of water. Among these wavelengths, the absorption wavelength bands of 1,340 to 1,480 nm and 1,800 to 2,100 nm have an especially high molar absorbance coefficient, and so these wavelength bands are preferably used. To this end, the light sources for near-infrared region may be a light source having a narrow wavelength region only, such as a LED or a semiconductor laser for near-infrared region.

TABLE 1

| quantum number at each level | | | |
|---|---|---|---|
| symmetrical stretch vibration $v1$ | bending vibration $v2$ | antisymmetric stretch vibration $v3$ | central wavelength of vibration band (nm) |
| 0 | 1 | 0 | 6274 |
| 0 | 2 | 0 | 3174 |
| 1 | 0 | 0 | 2735 |
| 0 | 0 | 1 | 2663 |
| 0 | 3 | 0 | 2143 |

TABLE 1-continued

| quantum number at each level | | | |
|---|---|---|---|
| symmetrical stretch vibration v1 | bending vibration v2 | antisymmetric stretch vibration v3 | central wavelength of vibration band (nm) |
| 1 | 1 | 0 | 1910 |
| 0 | 1 | 1 | 1875 |
| 1 | 2 | 0 | 1476 |
| 0 | 2 | 1 | 1455 |
| 2 | 0 | 0 | 1389 |
| 1 | 0 | 1 | 1379 |
| 0 | 0 | 2 | 1343 |
| 2 | 1 | 0 | 1141 |
| 1 | 1 | 1 | 1135 |
| 0 | 1 | 2 | 1111 |
| 3 | 0 | 0 | 943 |
| 2 | 0 | 1 | 942 |
| 1 | 0 | 2 | 920 |
| 0 | 0 | 3 | 906 |

The detection element for ultraviolet region desirably used is a silicon photodiode having high wavelength sensitivity in the ultraviolet region. The detection element for near-infrared region desirably used is an InGaAs photodiode or a PbS photodiode having high wavelength sensitivity in the near-infrared region. Those exemplified photodiodes have a large linearity range because it is used for liquid chromatography, and a photomultiplier may be used as the detection element. Alternatively, an array element including the array of a plurality of elements as in a silicon photodiode array or an InGaAs photodiode array may be used for this purpose.

The flow cell windows have to be made of a material of transmitting light from the ultraviolet region to the near-infrared region, and so synthetic silica is especially desirable for such a material. The eluent itself has high absorbance in the ultraviolet region and in the near-infrared region, and so the amount of baseline fluctuation is large, which may exceed the measurement range of the detector. Then, the flow cell preferably has an optical path length that is shorter than 10 mm that is a standard optical path length, which may be 1 mm appropriately, for example.

Figure 2:
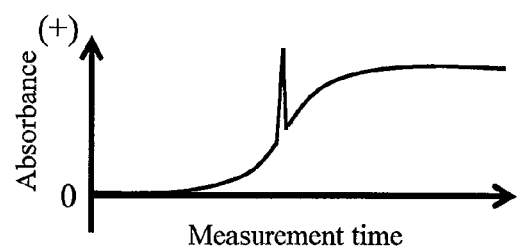
FIG. 2 describes an advantageous effect of the present invention.
Figure 2:
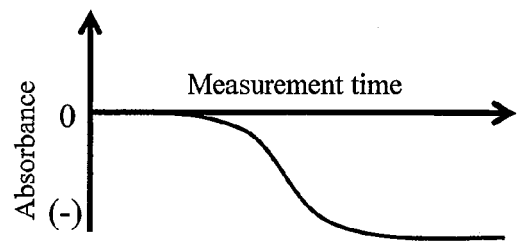
Figure 2:
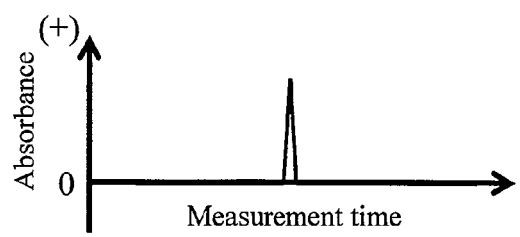

The configuration of FIG. 1 allows, during a gradient analysis in which the main component of the eluent changes from water to organic solvent, the first detection element that detects the light in the ultraviolet region to detect a synthesized value of a signal value resulting from the mobile phase and a signal value resulting from a sample, and allows the second detection element that detects the light in the near-infrared region to detect a signal value resulting from the mobile phase only as illustrated in FIG. 2. Combining these two signal values enables the removal of the signal value resulting from the mobile phase, whereby the signal value resulting from the sample only can be extracted. This method enables the two signal values to be obtained concurrently, and so a baseline fluctuation resulting from the mobile phase can be reduced in real time. Additionally, since a baseline fluctuation can be reduced in real time, the present method is applicable to any analysis condition without the necessity to acquire correction data in each case. Any method to combine the two signal values may be used, and from the viewpoint of simplicity for control, linear transformation as in the following expression, for example, is preferable:

$$f(t) = a \cdot U(t) + b \cdot N(t) \quad \text{[Expression 1]}$$

where
t: time,
f(t): signal value after correction,
U(t): signal value that is obtained by conversion of absorbance from the detection element in ultraviolet region;
N(t): signal value that is obtained by conversion of absorbance from the detection element in near-infrared region; and
a, b: factor.

The present invention is configured to introduce ultraviolet light and near-infrared light concurrently at the same time into the optical path of a common flow cell, and so their signal values are in phase, and so the correction shift due to time shift or the like, which is obtained from the linear transformation of signal values at a certain time, can be minimized.

Figure 3:
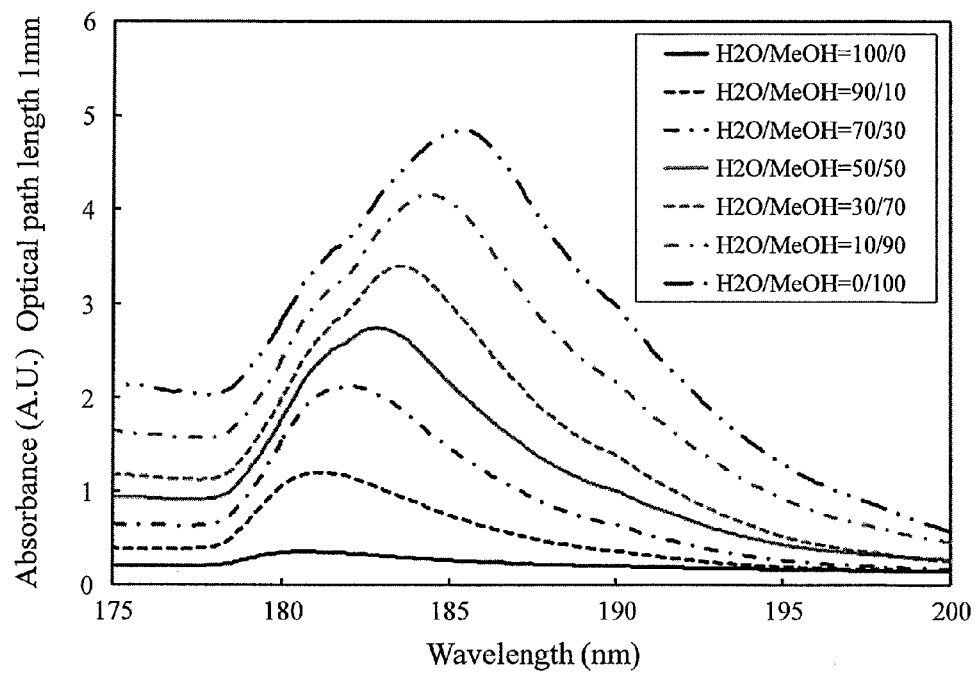
FIG. 3 illustrates an absorbance spectrum of a water/methanol mixing system in the ultraviolet region and the near-infrared region.
Figure 3:
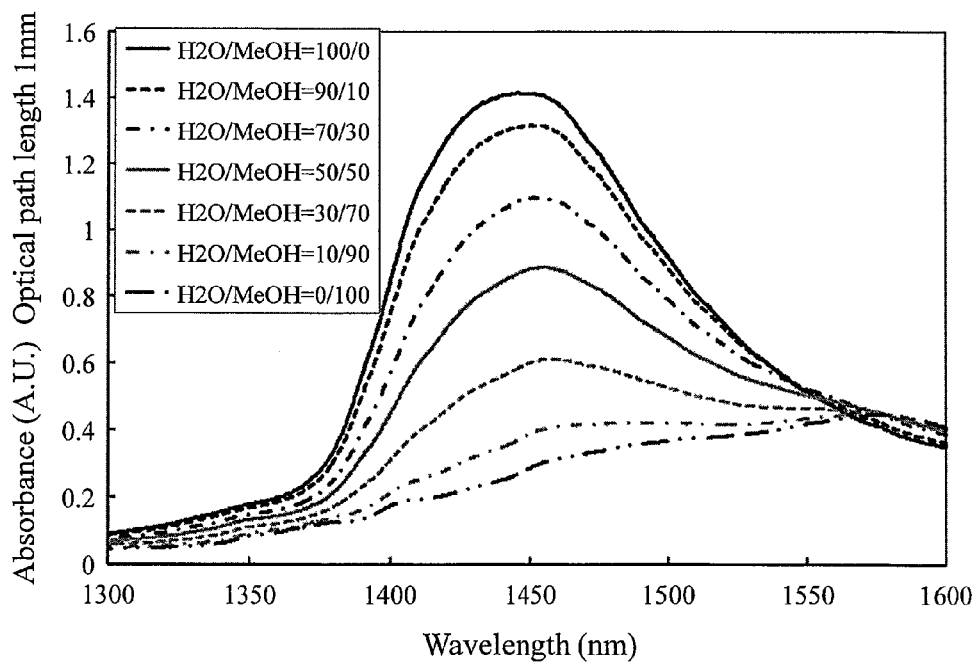

FIG. 3 illustrates an absorbance spectrum of a water/methanol mixing system in the ultraviolet region and the near-infrared region. As illustrated in FIG. 3, while the absorbance increases with the ratio of organic solvent in the water/organic solvent mixing system in the ultraviolet region, the absorbance decreases with an increase of the ratio of organic solvent in the water/organic solvent mixing system in the near-infrared region (this exemplifies a water/methanol system as a typical example). That is, as illustrated in FIG. 2, when the composition of the mobile phase successively changes from 100% of water to 100% of organic solvent, a signal value of the detection element in the ultraviolet region outputs a positive absorbance change, and the detection element in the near-infrared region outputs a negative absorbance change.

The configuration of the present invention can be used for the purpose to check whether the composition change of the mobile phase can be performed correctly as designed or not during a gradient analysis. In other words, this configuration can be used as a gradient monitor. That is, since the signal value from the detection element for light in the near-infrared region includes a signal value resulting from the mobile phase only, a baseline fluctuation value resulting from the mobile phase, especially a fluctuation value in association with the concentration ratio of water can be known. A conventional gradient monitor is configured based on the output value of a pressure sensor attached to a pump, because the viscosity changes with the concentration ratio of the mobile phase. Such a conventional gradient monitor, however, has the problem that, in the case of a water/organic solvent mixing system having a relationship between the viscosity and the concentration ratio of the mobile phase that does not increase or decrease monotonically but often has an extremum, the monitoring based on a pressure value is limited to the monitoring of a state of the overall pipe from the pump to the waste liquid. On the other hand, in the case of the gradient monitor based on the configuration of the present invention, the relationship between the concentration ratio of the mobile phase and the absorbance do not have an extremum, and increases or decreases monotonically, and a signal value on local information only at the position of the flow cell of the detector can be obtained, and so the disadvantage of the monitoring at the pump can be solved. At this time, the light in the ultraviolet region in the wavelength region where absorption resulting from the mobile phase does not exist may be used to detect a sample signal and perform gradient monitor only, or the light in the wavelength region where absorption resulting from the mobile phase exists may be used to reduce a baseline fluctuation in real time while performing gradient monitoring at the same time.

Figure 4:
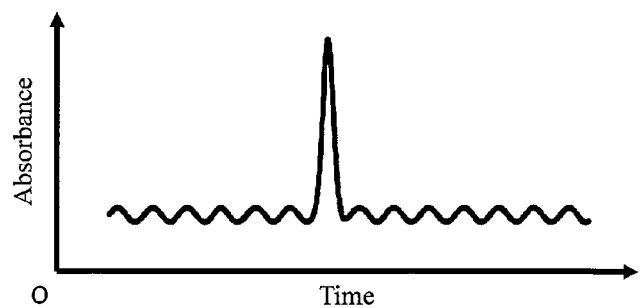
FIG. 4 describes an advantageous effect of the present invention.
Figure 4:
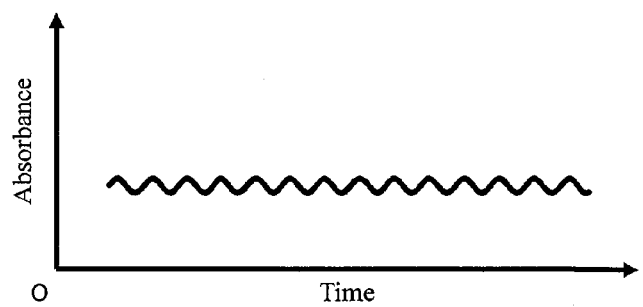
Figure 4:
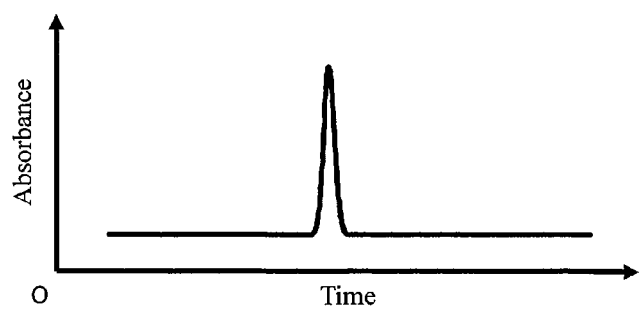

The present invention can reduce not only a baseline fluctuation resulting from the concentration of the mobile phase successively changing as stated above but also a baseline fluctuation (mixing ripple) due to a periodic concentration change of the concentration of the mobile phase resulting from the liquid sending by a pump. Under a condition of pump-mixing to create a certain concentration of eluent from two types of solution using a pump, since the mixing by liquid sending by the pump is not perfect, a baseline fluctuation in response to the liquid sending period of the pump is observed. This fluctuation poses a problem as baseline noise when eluent containing a substance having a high molar absorbance coefficient, e.g., trifluoroacetate is used. This phenomenon is observed in both of the gradient analysis where the concentration of the mobile phase changes successively and the isocratic analysis where the mobile phase is sent at a constant concentration value. At this time, the present invention allows a baseline fluctuation value in accordance with the concentration ratio of the mobile phase to be obtained from a signal value of light in the near-infrared region, and so based on a signal value resulting from the sample that is obtained from a signal value of light in the ultraviolet region and a mixture signal value of the baseline fluctuation value in accordance with the concentration ratio of the mobile phase, the baseline fluctuation value only can be removed as in FIG. 4 by Expression 1, for example, and so a high-sensitivity analysis can be achieved. This can be achieved by introducing light in the ultraviolet region and light in the near-infrared region to an optical path concurrently, thus matching the phase of the signal value from the first detection element with the signal value from the second element.

Figure 5:
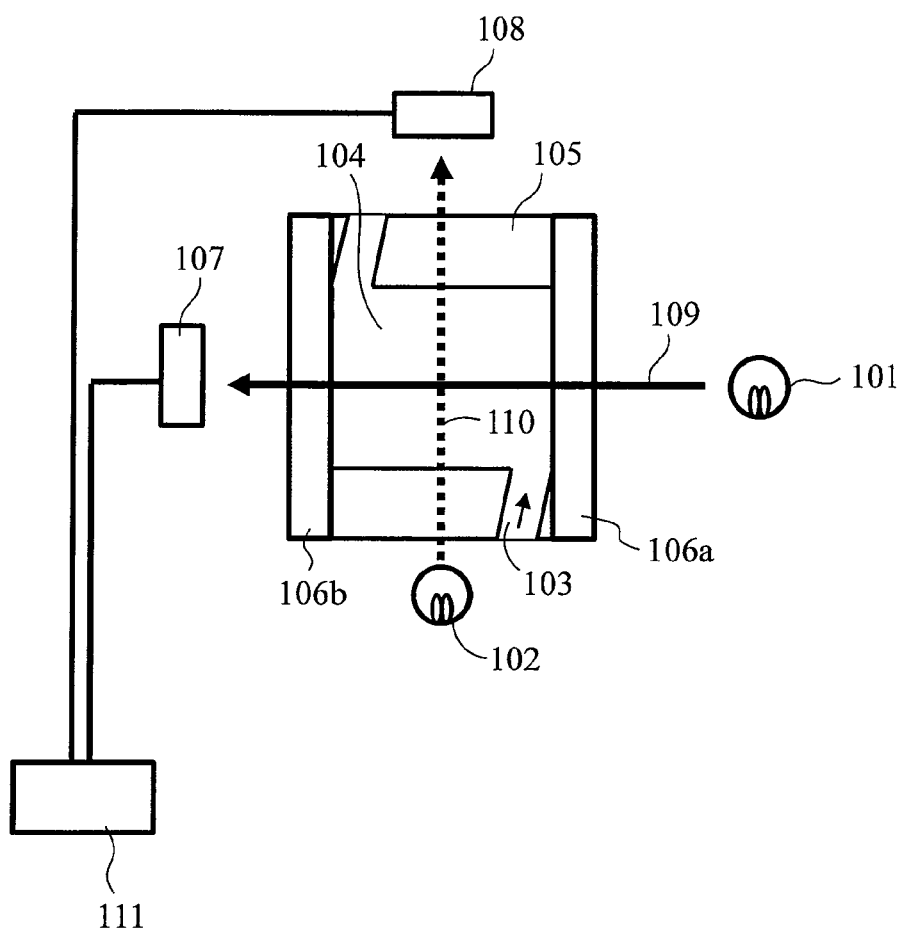
FIG. 5 schematically illustrates another embodiment of the detector for liquid chromatography according to the present invention.

FIG. 5 schematically illustrates another embodiment of the detector for liquid chromatography according to the present invention. The present embodiment includes the same components as those of the embodiment illustrated in FIG. 1, but the light source 102 for near-infrared region and the detection element 108 for near-infrared region are disposed to be orthogonal to the channel direction of the flow cell 105. This disposition enables detection of ultraviolet light and near-infrared light independently without separating them. This disposition further enables different optical path lengths to be set for ultraviolet light and near-infrared light with one flow cell. That is, when a channel 104 has a cylindrical shape of 1 mm in diameter and 10 mm in length, such a flow cell has an optical path length of 10 mm for the ultraviolet light and an optical path length of 1 mm for the near-infrared light. This disposition allows the detection in the ultraviolet region with the optical path length of 10 mm that is equal to the conventional one, to which a gradient monitor function can be added by the detection in the near-infrared region. In this disposition, the flow cell 105 has to be made of a material of transmitting the near-infrared light, and so synthetic silica or silicon is desirably used, for example. It is preferably coated with diamond-like carbon, for example, at the inner wall surface so as to reduce scattering of the ultraviolet light reflected at the inner wall of the flow cell.

Figure 6:
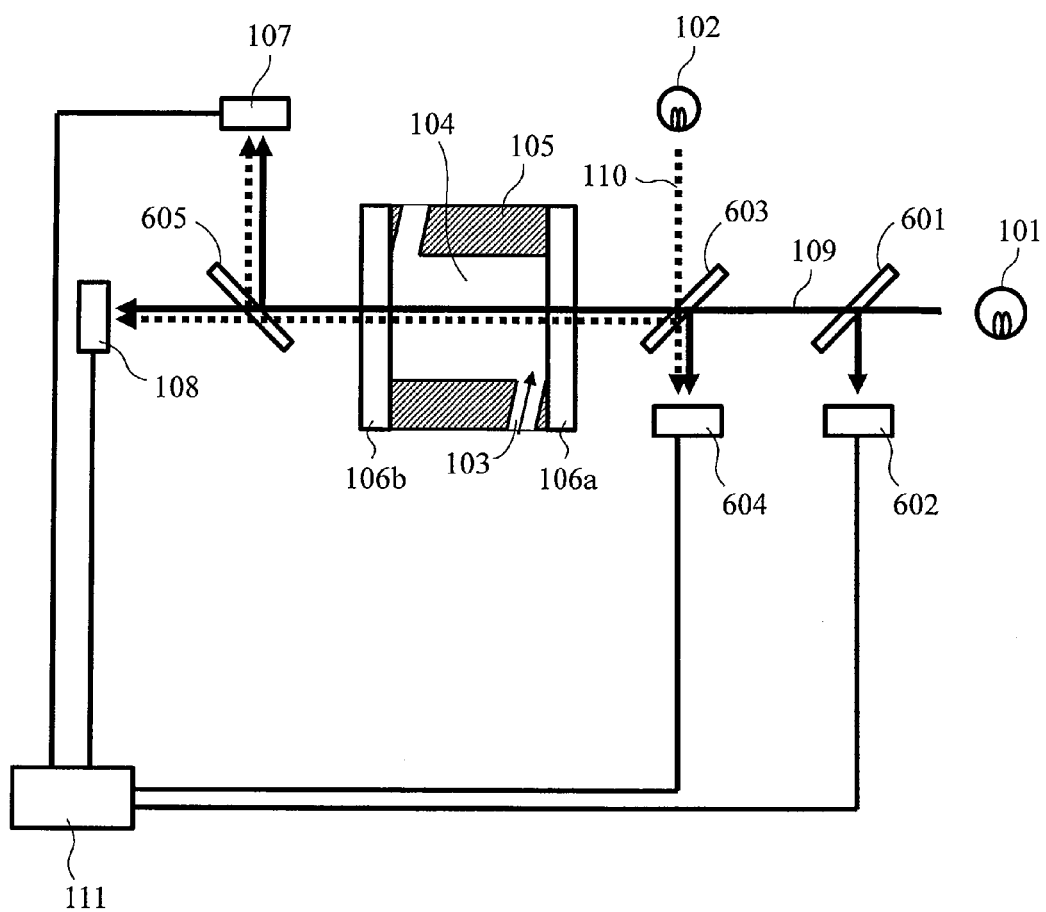
FIG. 6 schematically illustrates still another embodiment of the detector for liquid chromatography according to the present invention.

FIG. 6 schematically illustrates still another embodiment of the detector for liquid chromatography according to the present invention. The present embodiment includes, in addition to the configuration of FIG. 1, a half mirror 601 and a detection element for ultraviolet region 602 to divide ultraviolet light before passing through the flow cell for detection, a half mirror 603 and a detection element for near-infrared region 604 to divide near-infrared light before passing through the flow cell for detection, and a half mirror 605 to divide light after passing through the flow cell. Since different light sources are used for the ultraviolet region and the near-infrared region, they do not agree in the period of fluctuations of the light sources (light-intensity fluctuations, light-spot fluctuations and the like), and so such fluctuations influence to increase noise. Then the detection elements for reference, which correspond to the light sources, are disposed before passing through the flow cell, thus monitoring the intensity of the light sources as illustrated in FIG. 6. In this way, a signal value including the fluctuations of the light sources is obtained, which is combined with signal values obtained from the detection element 107 for ultraviolet region and the detection element 108 for near-infrared region to detect light after passing through the flow cell, whereby a signal value, from which the fluctuations of the light sources can be removed, can be calculated.

In the exemplary configuration of FIG. 6, ultraviolet light and near-infrared light are applied at the same time to the detection elements 107, 108 and 604, and ultraviolet light and near-infrared light can be selectively detected by appropriately selecting the sensing wavelengths of the detection elements used. That is, a silicon photodiode having a sensing wavelength of 160 nm to 1,100 nm may be used as the detection element for ultraviolet light, whereby ultraviolet light only can be detected without responding to near-infrared light. Similarly, an InGaAs photodiode having a sensing wavelength of 900 nm to 2,500 nm may be used as the detection element for near-infrared light, whereby near-infrared light only can be detected without responding to ultraviolet light. As a result, ultraviolet light and near-infrared light can be selectively detected. Preferably the half mirrors may include a substrate that is made of synthetic silica having high transmittance from the ultraviolet region to the near-infrared region, and a coating film that is made of aluminum or a dielectric multilayer having high reflectivity from the ultraviolet region to the near-infrared region.

In this exemplary configuration, light emitted from the light sources is used without splitting, because organic solvent has a wide absorption wavelength band in the ultraviolet region and water has a wide absorption wavelength band in the near-infrared region, and so a response resulting from each solvent can be detected without splitting, which leads to another advantage that the light does not attenuate because it is not split, and the total light amount becomes large. Instead of the half mirror, a dichroic mirror or the like may be used as the optical resolution element. Such an element, however, is not made of a material that, when any one of the ultraviolet wavelength and the near-infrared wavelength is reflected, can transmit the light of the wavelength that is not reflected effectively, and so has difficulty to achieve the splitting of both of the ultraviolet wavelength and the near-infrared wavelength effectively. In this way, the dichroic mirror is not suitable for the detector of the present invention.

In the embodiment illustrated in FIG. 6, arithmetic processing of Expression 2 may be performed to the signal value obtained, whereby noise can be reduced. The signal value after passing through the flow cell is processed using the signal value before passing through the flow cell as in the present embodiment, whereby fluctuations resulting from the light sources can be removed, and so noise of a corrected value, which is obtained after combining the signal value in the ultraviolet region and the signal value in the near-infrared region from different light sources, can be suppressed.

$$f(t)=a(US(t)-UR(t))+b(NS(t)-NR(t))$$

where t: time;

f(t): signal value after correction;

US(t): signal value subjected to absorbance conversion, which is obtained from the detection element in ultraviolet region after passing through flow cell;

UR(t): signal value subjected to absorbance conversion, which is obtained from the detection element in ultraviolet region before passing through flow cell;

NS(t): signal value subjected to absorbance conversion, which is obtained from the detection element in near-infrared region after passing through flow cell;

NR(t): signal value subjected to absorbance conversion, which is obtained from the detection element in near-infrared region before passing through flow cell; and a, b: factor.

Figure 7:
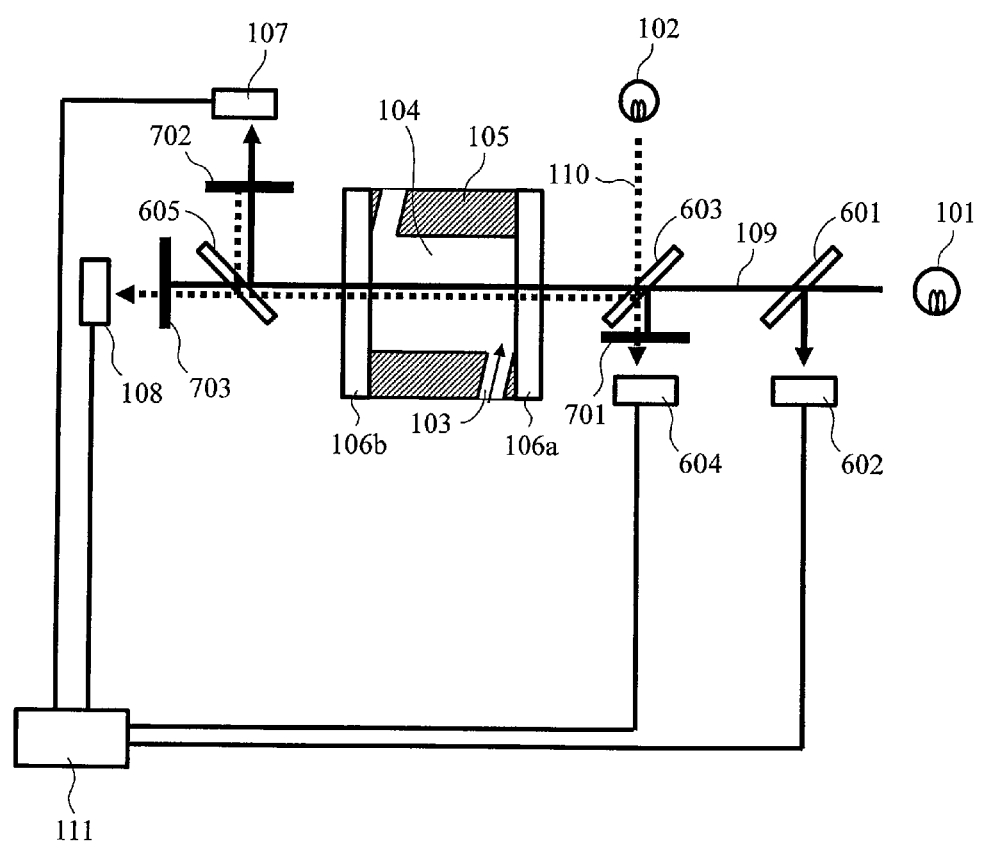
FIG. 7 schematically illustrates a further embodiment of the detector for liquid chromatography according to the present invention.

FIG. 7 schematically illustrates a further embodiment of the detector for liquid chromatography according to the present invention. The present embodiment includes an ultraviolet region transmission filter 702 and near-infrared region transmission filters 701, 703 disposed immediately before the corresponding detectors, in addition to the exemplary configuration of FIG. 6. The thus disposed filters that selectively transmit ultraviolet light or near-infrared light only can eliminate the effect that light that is not converted into electrons at each detection element is converted into heat, thus causing temperature fluctuations, and amplifying signal noise. The ultraviolet region transmission filter may be made of a material that transmits ultraviolet light and absorbs near-infrared light, and so a commercially available short path filter or band path filter for ultraviolet region, water enclosed in a synthetic silica cell or the like may be used for the purpose. The near-infrared region transmission filter may be made of a material that absorbs ultraviolet light and transmits near-infrared light, and so a commercially available long path filter or band path filter for near-infrared region, a silicon substrate or the like may be used for the purpose.

Figure 8:
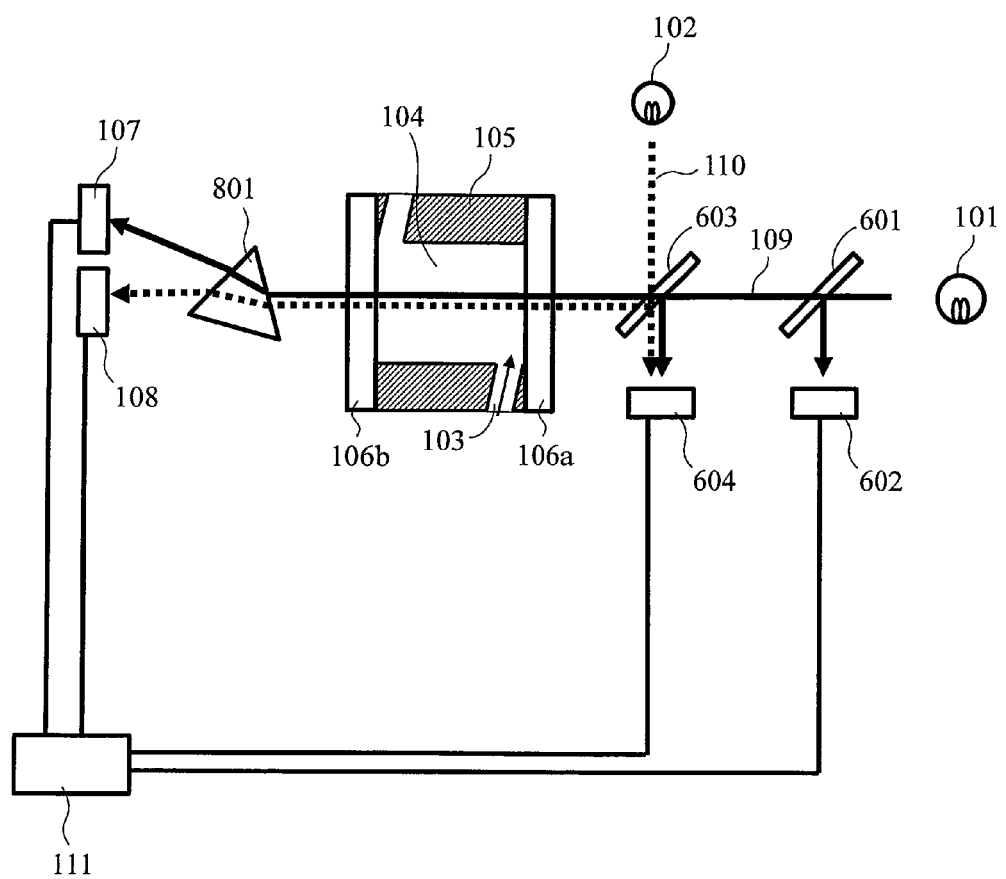
FIG. 8 schematically illustrates a still further embodiment of the detector for liquid chromatography according to the present invention.

FIG. 8 schematically illustrates a still further embodiment of the detector for liquid chromatography according to the present invention. The present embodiment includes a spectroscope 801 instead of the half mirror 605 disposed on the optical path after passing through the flow cell, and a detection element to detect light the split light downstream of the spectroscope in the exemplary configuration of FIG. 6. The system including a half mirror to split light can simplify the optical system, but has the disadvantage that, since ultraviolet light and near-infrared light are divided into reflected light and transmitted light, and so the amount of light attenuates. On the other hand, the system including a spectroscope to divide light can carry ultraviolet light and near-infrared light effectively to the detection element. A diffractive grating is typically designed so as to split light effectively around a certain wavelength, and has difficulty in effectively splitting the ultraviolet light the near-infrared light effectively. Then, a method to split light using a prism made of synthetic silica based on a difference in refractive index is more efficient and preferable. Further light other than the sensing wavelength of the detection element will not be carried to the detection element because of splitting light, and so influences of thermal fluctuations from thermal energy can be reduced.

Figure 9:
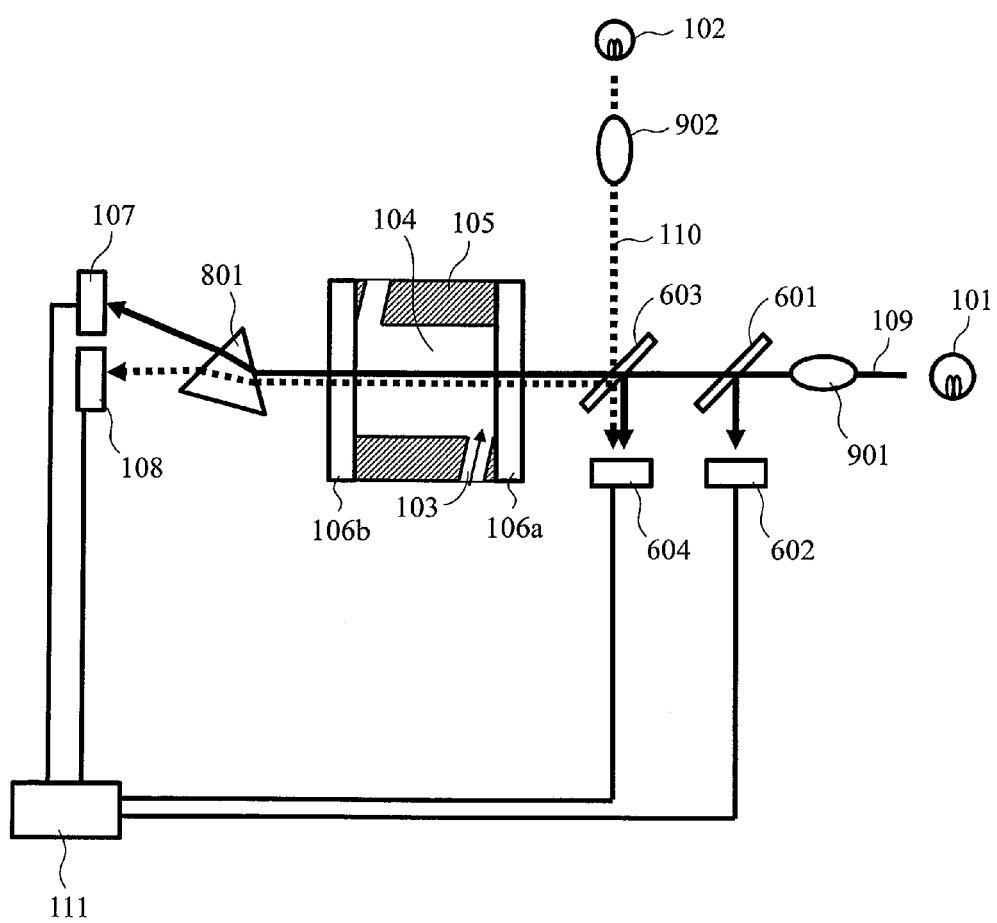
FIG. 9 schematically illustrates another embodiment of the detector for liquid chromatography according to the present invention.

FIG. 9 schematically illustrates another embodiment of the detector for liquid chromatography according to the present invention. The present embodiment includes a spectroscope for ultraviolet region 901 and a spectroscope for near-infrared region 902 immediately after the corresponding light sources in the exemplary configuration of FIG. 8, so that monochromatic light can be introduced into the optical system of FIG. 8. In this way, monochromatic light that is split beforehand is introduced into the optical system, whereby a signal value of an effective wavelength only can be selected, and so extraction of a sample signal and reduction of a baseline fluctuation can be performed effectively. Further since the light is split beforehand, influences of thermal fluctuations from thermal energy can be minimized at the detection elements. When a semiconductor laser or a LED is used as the light sources, a light beam emitted is close to monochrome light, and so the spectroscope does not always have to be disposed immediately after the light sources. In the example of FIG. 9, although the spectroscopes are disposed immediately after both of the light sources for ultraviolet region and near-infrared region, the spectroscope may be disposed at any one of them.

Figure 10:
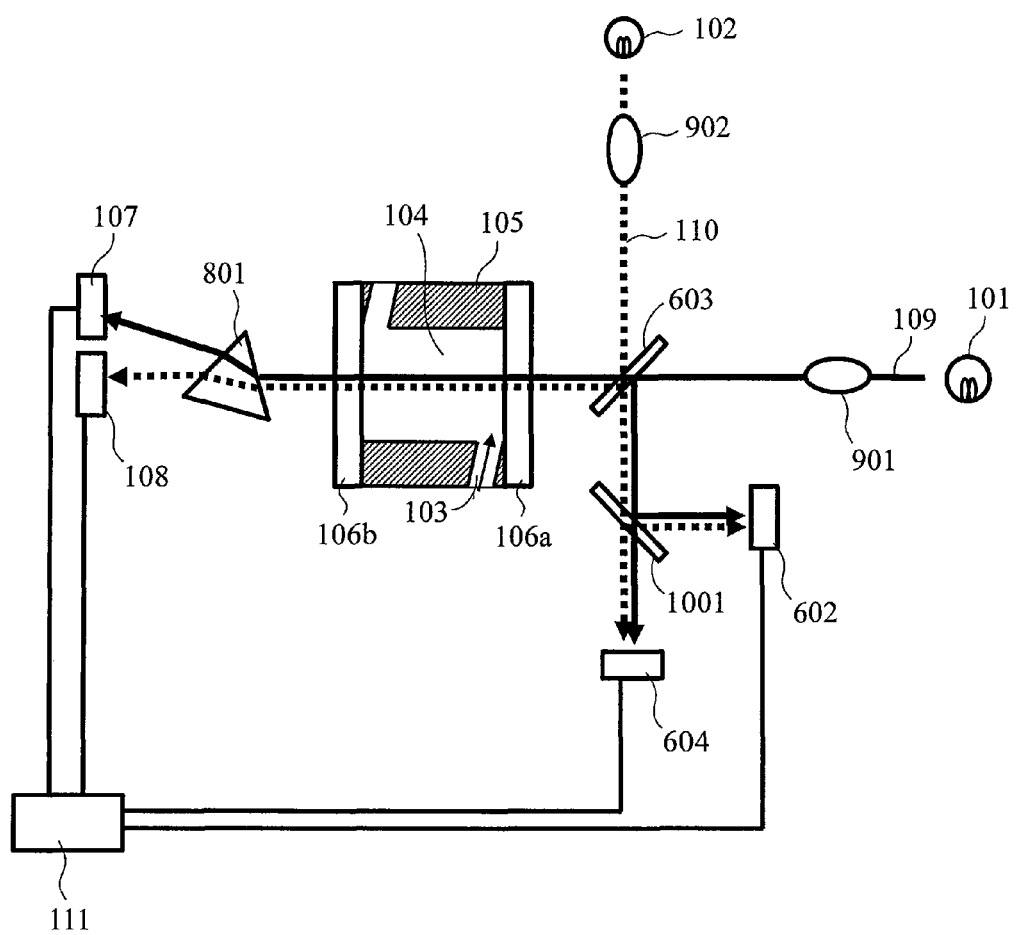
FIG. 10 schematically illustrates still another embodiment of the detector for liquid chromatography according to the present invention.

FIG. 10 schematically illustrates still another embodiment of the detector for liquid chromatography according to the present invention. The present embodiment includes a half mirror 1001, which is disposed instead of the half mirror 601 of the exemplary configuration of FIG. 9. In this way a light beam is split after the ultraviolet light and the near-infrared light merge, whereby the optical system to the detection elements can be made common, and so influences from fluctuations resulting from the optical system can be minimized, and so signal noise can be reduced.

Figure 11:
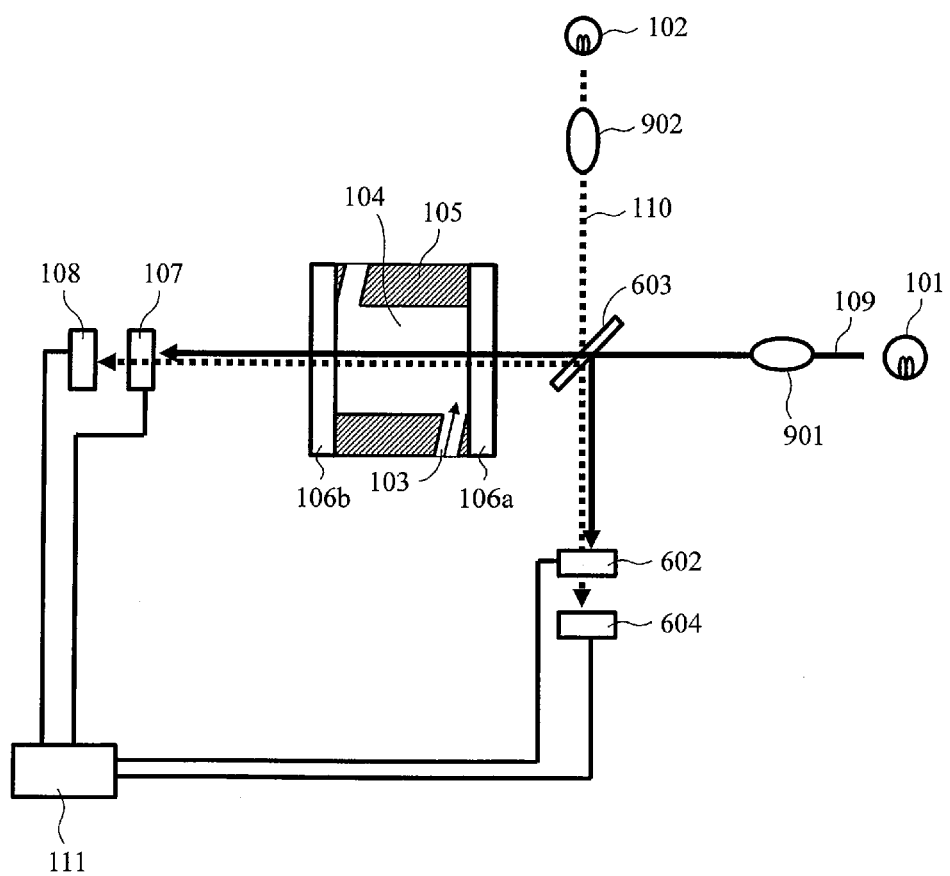
FIG. 11 schematically illustrates a further embodiment of the detector for liquid chromatography according to the present invention.

FIG. 11 schematically illustrates a further embodiment of the detector for liquid chromatography according to the present invention. The present embodiment does not include the half mirror 601 and the spectroscope 801 in the exemplary configuration of FIG. 9, and disposes the ultraviolet region detection elements 107 and 602 upstream and the near-infrared region detection elements 108 and 604 downstream to be a serial arrangement. That is, the near-infrared detection element 108 is disposed behind the ultraviolet detection element 107, and the near-infrared detection element 604 is disposed behind the ultraviolet-region detection element 602. The ultraviolet-region detection element used is a photodiode that can transmit light in the near-infrared region, whereby such a configuration is enabled. For instance, a transmission-type silicon photodiode is desirably used as such a detection element. This configuration can reduce the number of optical components and can minimize fluctuations resulting from the optical system, and can carry the amount of light to the detection element effectively because there is no need to split light.

These embodiments exemplify a half mirror as means to split a light beam, and an optical element that switches the reflection of a light beam at a high frequency can be used. For instance, a wheel-type chopper including a mirror and a gap at the surface or an element provided with a small mirror array that is manufactured by a MEMS technique may be used. Since a liquid chromatography product that is a major application of the present invention has a sampling internal during a high-speed analysis of about a few hundreds Hz, these elements may be used so as to operate at the rate sufficiently higher than that. For instance, these elements may operate at the frequency of about a few kHz, for example, whereby a pulse-like change can be flattened when a detection element picks up a signal value as if light can be constantly split.

These embodiments exemplify a photodiode that detects a single wavelength only. Meanwhile, a spectroscope may be introduced after the half mirror 605 of FIG. 6, for example, for post-splitting, and a photodiode array may be provided as the detection element, whereby information on a plurality of wavelengths can be obtained. In that case, a signal value vector obtained from the detection element for ultraviolet region and a signal value vector obtained from the detection element for near-infrared region are preferably combined as in the following Expression (3):

$$f(t) = A \cdot U + B \cdot N \quad \text{[Expression 3]}$$

$$= \begin{pmatrix} a_1 \\ \vdots \\ a_n \end{pmatrix} \cdot \begin{pmatrix} U_1(t) \\ \vdots \\ U_n(t) \end{pmatrix} + \begin{pmatrix} b_1 \\ \vdots \\ b_n \end{pmatrix} \cdot \begin{pmatrix} N_1(t) \\ \vdots \\ N_n(t) \end{pmatrix}$$

where
t: time;
f(t): signal value after correction;
U: signal value vector subjected to absorbance conversion, which is obtained from the detection element in ultraviolet region;
N: signal value vector subjected to absorbance conversion, which is obtained from the detection element in near-infrared region;
$U_1(t) \ldots U_n(t)$: signal value of each wavelength subjected to absorbance conversion, which is obtained from the detection element in ultraviolet region;
$N_1(t) \ldots N_n(t)$: signal value of each wavelength subjected to absorbance conversion, which is obtained from the detection element in near-infrared region;
A, B: factor matrix; and
$a_1 \ldots a_n, b_1 \ldots b_n$: factor.

The following describes exemplary experiments to verify the effects from the present invention.

Figure 12:
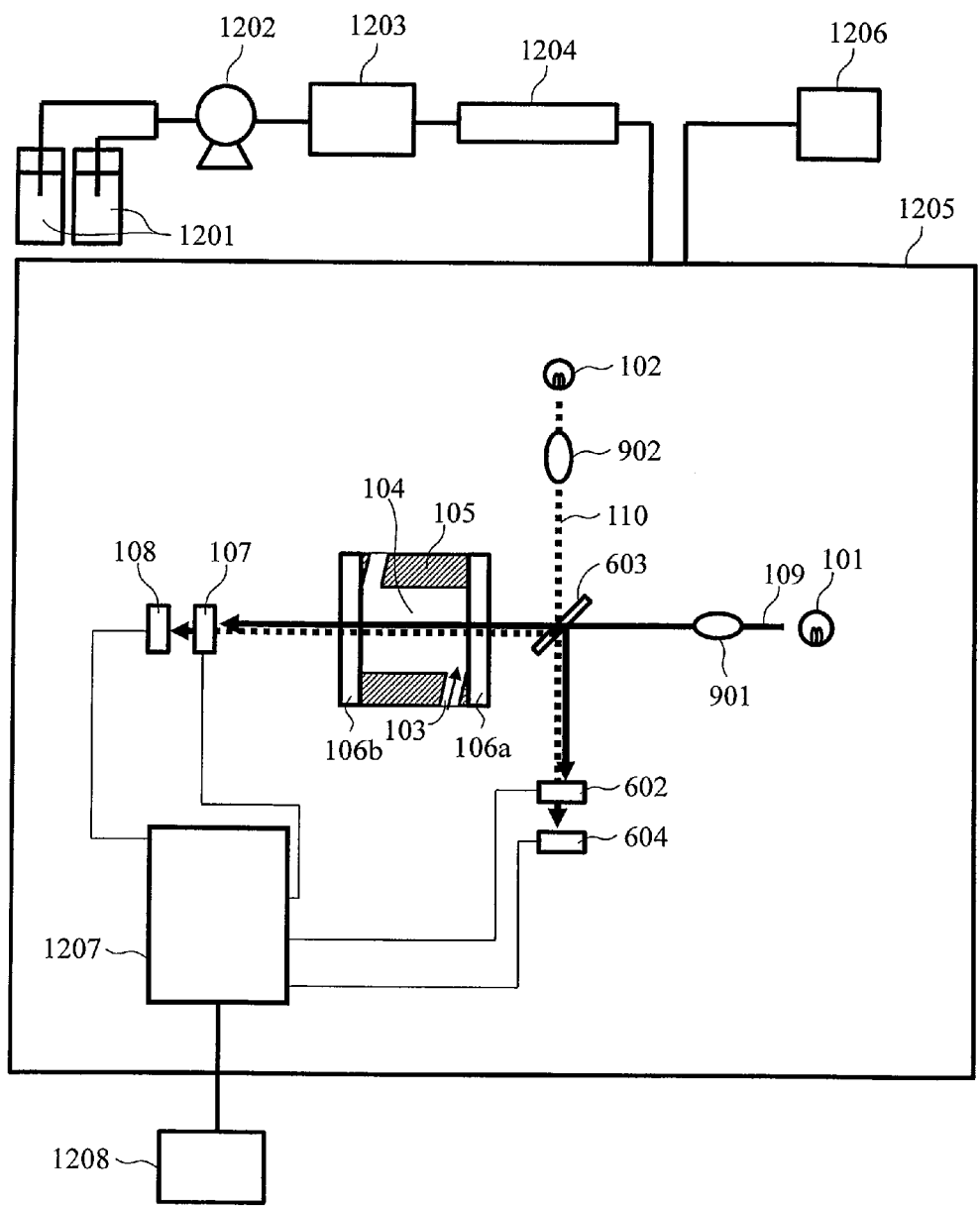
FIG. 12 schematically illustrates a liquid chromatographic system including a decoder of the present invention incorporated therein.

FIG. 12 schematically illustrates a liquid chromatographic system including a decoder of the present invention incorporated therein. FIG. 12 shows a low-pressure gradient sending type liquid chromatogram system, including eluent 1201, a pump 1202, an auto sampler 1203, a column 1204, a detector 1205 and a waste liquid container 1206. The detector 1205 for liquid chromatography includes the configuration of the embodiment of FIG. 11 therein, in which an arithmetic processing unit 1207 processes a signal value obtained from the detection elements and outputs a resultant to an external controller 1208.

Liquid was sent at the rate of 1.0 ml/min. (10 MPa) in the low-pressure gradient mode, and a gradient analysis was performed, in which the composition of the mobile phase was linearly changed in six minutes from the mixture solution of 20% of water and 80% of acetonitrile to 40% of water and 60% of acetonitrile. Light split at 185 nm and light split at 1,450 nm were introduced as the light in ultraviolet region and the light in near-infrared region, respectively, into the flow cell 105. The analytical column used was a column produced by YMC cooperation (YMC-Pack, Polyamine•II, 4.6 mm×150 mm column), and 10 μL of mixture aqueous solution of 100 ppm in concentration, containing fructose, glucose and sucrose was introduced as a sample. The flow cell had an optical path length of 1 mm. Signal values obtained from the detection elements for ultraviolet region and near-infrared region were processed so as to subtract signal values obtained from the detection elements for reference as in Expression 2, thus removing influences from fluctuations at the light sources. Then, the signal value for ultraviolet region, from which the influences from light-source fluctuations have been removed, was multiplied by the factor 1, and the signal value for near-infrared region similarly processed was multiplied by the factor 0.2, which were then added, thus finding a signal value as the final data value.

Figure 13:
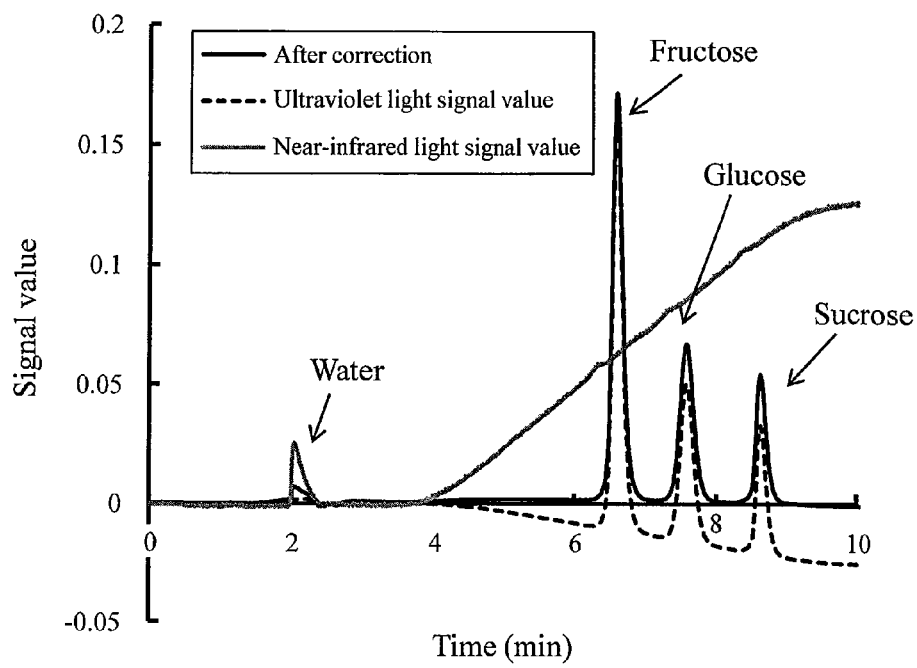
FIG. 13 illustrates a result indicating that a baseline fluctuation during a gradient analysis was reduced by the detector for liquid chromatography of the present invention.

FIG. 13 illustrates a result indicating that a baseline fluctuation during a gradient analysis were reduced by the detector for liquid chromatography of the present invention. Since the ratio of water to the organic solvent was increased in the condition of FIG. 13, positive and negative signs are reversed from the schematic illustration of FIG. 2. As illustrated in FIG. 13, it was confirmed that a signal value in the ultraviolet region and a signal value in the near-infrared region are combined, whereby a great baseline fluctuation resulting from the mobile phase can be reduced.

Figure 14:
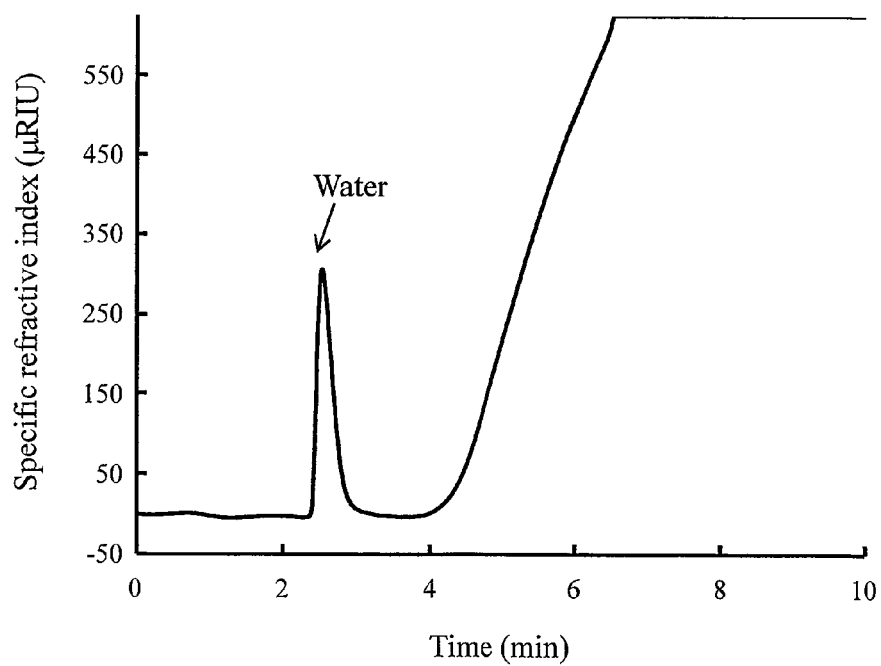
FIG. 14 illustrates a signal value during a gradient analysis using a conventional differential refractive index detector.
Figure 15:
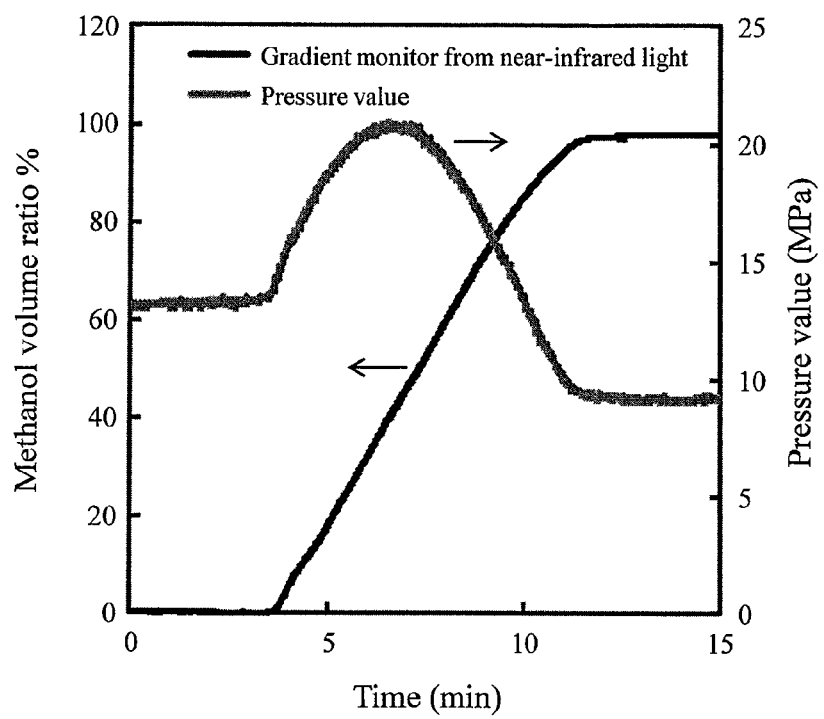
FIG. 15 illustrates the result of the ratio of methanol in the mobile phase during a gradient analysis that was found using the detector for liquid chromatography of the present invention.

FIG. 14 illustrates the result obtained when an analysis was performed using a differential refractive index detector as a conventional universal detector under a similar condition. As can be seen from FIG. 14, the analysis performed using the differential refractive index detector had a large baseline fluctuation resulting from the mobile phase, and the gradient analysis was not conducted successfully because the data became saturated before obtaining a sample signal value. Comparison between FIG. 13 and FIG. 14 shows the effectiveness of the present invention. For verification whether the ratio of organic solvent can be detected during the gradient analysis, FIG. 15 illustrates the result of real-time calculation of the ratio of methanol during the gradient analysis (the composition changed from 100% water to 100% methanol) using data obtained beforehand about a standard curve showing the relationship of a signal value and a concentration ratio of water-organic solvent from a signal value of light in the near-infrared region. FIG. 15 shows the output values of the pressure sensor attached to the pump as well. As can be seen from FIG. 15, the state where the concentration ratio of water-organic solvent increases monotonically with time can be monitored by the gradient analysis. Note that, although FIG. 12 shows a driving example in the low-pressure gradient mode, a similar effect will be obtained from a driving example in the high-pressure gradient mode as well.

The above embodiments exemplify how to combine a signal value obtained from ultraviolet light and a signal value obtained from near-infrared light using Expressions 1, 2 and 3 because they prioritize a real-time analysis. Needless to say, a baseline fluctuation can be reduced by any combination method other than this. For instance, the relationship between a water-organic solvent ratio and absorbance in the mobile phase is found beforehand in the ultraviolet region and the near-infrared region, and the relationship may be processed by fitting using polynomial approximation, for example, whereby any combination method can be produced.

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced.

DESCRIPTION OF SYMBOLS

101: Ultraviolet region light source
102: Near-infrared region light source
103: Sample liquid
104: Flow cell channel
105: Flow cell
106a, 106b: Flow cell window
107, 602: Detection element for ultraviolet region 108, 604: Detection element for near-infrared region
109: Ultraviolet light
110: Near-infrared light
111, 1207: Arithmetic operation part
601, 603, 605, 1001: Half mirror
701, 702, 703: Filter
801, 901, 902: Spectroscope
1201: Eluent
1202: Pump
1203: Auto sampler
1204: Column
1205: Detector
1206: Waste liquid container
1208: External controller

What is claimed is:

1. A detector for liquid chromatography, comprising:
a first light source that generates light in an ultraviolet region;
a second light source that generates light in a near-infrared region;
a flow cell, through which sample liquid flows;
an optical system to let light generated from the first light source and light generated from the second light source incident on the flow cell concurrently;
a first detection element that detects light in the ultraviolet region that passes through the flow cell;
a second detection element that detects light in the near-infrared region that passes through the flow cell; and
an arithmetic operation part that performs arithmetic operation of a first signal value obtained from the first detection element and of a second signal value obtained from the second detection element.

2. The detector for liquid chromatography according to claim 1, wherein
the sample liquid includes water as one component, and the water has concentration that changes successively with time.

3. The detector for liquid chromatography according to claim 2, wherein
the arithmetic operation part combines the first signal value and the second signal value to reduce a baseline fluctuation resulting from a mobile phase during a gradient analysis.

4. The detector for liquid chromatography according to claim 2, wherein
the arithmetic operation part calculates a signal value f(t) with a reduced baseline fluctuation resulting from the mobile phase during the gradient analysis by the following expression, $$f(t)=a \cdot U(t)+b \cdot N(t)$$

where
t denotes time, U(t) denotes a signal value that is subjected to conversion of absorbance obtained from the first detection element, N(t) denotes a signal value that is subjected to conversion of absorbance obtained from the second detection element, and a and b denote factors.

5. The detector for liquid chromatography according to claim 2, further comprising a third detection element to monitor intensity of light generated from the first light source, and a fourth detection element to monitor intensity of light generated from the second light source, wherein
the arithmetic operation part calculates a signal value f(t) with a reduced baseline fluctuation resulting from the mobile phase during the gradient analysis by the following expression, $$f(t)=a(US(t)-UR(t))+b(NS(t)-NR(t))$$

where
t denotes time, US(t) denotes a signal value subjected to absorbance conversion, which is obtained from the first detection element, UR(t) denotes a signal value subjected to absorbance conversion, which is obtained from the third detection element, NS(t) denotes a signal value subjected to absorbance conversion, which is obtained from the second detection element; NR(t) denotes a signal value subjected to absorbance conversion, which is obtained from the fourth detection element, and a and b denote factors.

6. The detector for liquid chromatography according to claim 2, wherein
the first detection element and the second detection element are photodiode arrays, and
the arithmetic operation part calculates a signal value f(t) with a reduced baseline fluctuation resulting from the mobile phase during the gradient analysis by the following expression, $$f(t) = A \cdot U + B \cdot N$$
$$= \begin{pmatrix} a_1 \\ \vdots \\ a_n \end{pmatrix} \cdot \begin{pmatrix} U_1(t) \\ \vdots \\ U_n(t) \end{pmatrix} + \begin{pmatrix} b_1 \\ \vdots \\ b_n \end{pmatrix} \cdot \begin{pmatrix} N_1(t) \\ \vdots \\ N_n(t) \end{pmatrix}$$

where
t denotes time, U denotes a first signal value vector including information on a plurality of wavelengths obtained from the first detection element, N denotes a signal value vector subjected to absorbance conversion, which is obtained from the second detection element, $U_1(t) \ldots U_n(t)$ denotes a signal value of each wavelength subjected to absorbance conversion, which is obtained from the first detection element, $N_1(t) \ldots N_n(t)$ denotes a signal value of each wavelength subjected to absorbance conversion, which is obtained from the second detection element, A and B denote factor matrices, and $a_1 \ldots a_n$ and $b_1 \ldots b_n$ denote factors.

7. The detector for liquid chromatography according to claim 1, wherein
light in the ultraviolet region and light in the near-infrared region that pass through the flow cell proceed along a same optical path, which is divided into two by an optical splitting element, a silicon photodiode is disposed as the first detection element on one of the two-divided optical paths, and an indium-gallium-arsenide photodiode or a lead sulfide photodiode is disposed as the second detection element on the other optical path.

8. The detector for liquid chromatography according to claim 1, wherein
light in the ultraviolet region and light in the near-infrared region that pass through the flow cell proceed along a same optical path, which is divided into two by an optical splitting element, an ultraviolet region transmission filter and the first detection element are disposed on one of the two-divided optical paths, and a near-infrared region transmission filter and the second detection element are disposed on the other optical path.

9. The detector for liquid chromatography according to claim 1, wherein
an optical path of light generated from the first light source and an optical path of light generated from the second light source intersect in the flow cell.

10. The detector for liquid chromatography according to claim 1, further comprising:
a first spectroscope that splits light generated from the first light source and/or a second spectroscope that splits light generated from the second light source, and
light at a specific wavelength in the ultraviolet region split by the first spectroscope and/or light at a specific wavelength in the near-infrared region split by the second spectroscope are allowed to be incident on the flow cell.

11. The detector for liquid chromatography according to claim 5, wherein
the first detection element and the third detection element are transmission-type silicon photodiodes that can transmit light in the near-infrared region, where the second detection element is disposed behind the first detection element, and the fourth detection element is disposed behind the third detection element.

* * * * *